United States Patent [19]

Dorlars et al.

[11] 4,217,449
[45] Aug. 12, 1980

[54] PROCESS FOR THE PREPARATION OF BIS-TRIAZOLYLSTILBENES

[75] Inventors: Alfons Dorlars, Leverkusen; Otto Neüner, Berg. Gladbach, both of Fed. Rep. of Germany

[73] Assignee: Bayer Aktiengesellschaft, Leverkusen, Fed. Rep. of Germany

[21] Appl. No.: 950,438

[22] Filed: Oct. 11, 1978

[30] Foreign Application Priority Data

Oct. 13, 1977 [DE] Fed. Rep. of Germany ....... 2746000

[51] Int. Cl.$^2$ .......................................... C07D 249/06
[52] U.S. Cl. ...................................542/462; 548-255
[58] Field of Search ..................... 260/308 A; 542/462

[56] References Cited

U.S. PATENT DOCUMENTS

| | | | |
|---|---|---|---|
| 3,666,758 | 5/1972 | Dorlars et al. | 542/462 |
| 3,928,329 | 12/1975 | Fleck et al. | 542/462 |
| 3,947,412 | 3/1976 | Claussen | 260/308 A |
| 3,965,094 | 6/1976 | Claussen et al. | 542/462 |
| 4,005,098 | 1/1977 | Dorlars et al. | 260/308 A |

OTHER PUBLICATIONS

D'Olieslager et al., Bull. Soc. Chim., France, 1967, #1, pp. 179–188.

*Primary Examiner*—Arthur P. Demers
*Attorney, Agent, or Firm*—Sprung, Felfe, Horn, Lynch & Kramer

[57] ABSTRACT

Process for the preparation of bis-triazolylstilbene compounds which, in the form of the free acid, correspond to the formula

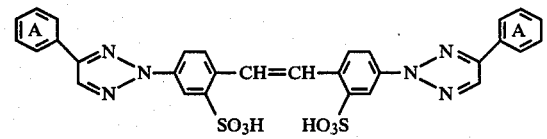

wherein
the phenyl radicals A can be substituted by halogen, $C_1$–$C_4$-alkyl or $C_1$–$C_4$-alkoxy, from bis-hydroxyiminohydrazonostilbene compounds of the formula

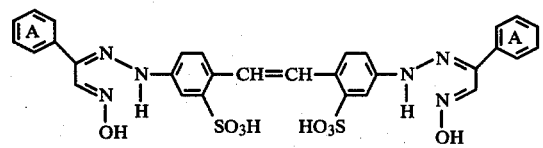

characterized in that the bis-hyroxyiminohydrazonostilbene compounds are reacted with anhydrides of lower carboxylic acids in the presence of urea and polar solvents at temperatures from 10° to 60° C.

2 Claims, No Drawings

PROCESS FOR THE PREPARATION OF BIS-TRIAZOLYLSTILBENES

The invention relates to a process for the preparation of bis-triazolylstilbenes which, in the form of the free acid, correspond to the formula

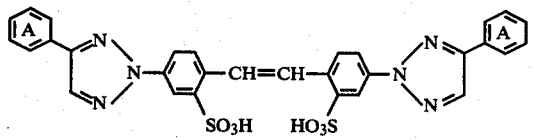

wherein
the phenyl radicals A can be substituted by halogen, $C_1$–$C_4$-alkyl or $C_1$–$C_4$-alkoxy.

Suitable halogen is bromine and, in particular, chlorine.

The process is preferably used for the preparation of the compound in which the phenyl radicals A are not further substituted.

The compounds of the formula (I) are known as optical brighteners from German Pat. No. 1,279,636 (U.S. Pat. No. 3,485,831). They are prepared by a condensation reaction of 4,4'-dihydrazinostilbene-2,2'-disulphonic acid with α-hydroxyiminomethyl ketones, isolation and drying of the bis-(hydroxyiminohydrazono)-stilbenedisulphonic acids formed and subsequent cyclisation thereof, water being split off. In the abovementioned German patent specification, the cyclisation is carried out with a 30-fold to 40-fold molar excess (relative to bis-(hydroxyiminohydrazono)-stilbenedisulphonic acid) of acetic anhydride as the suspension medium, in the presence of sodium acetate and small amounts of dimethylformamide, the mixture being heated to 105° C. for about 8 hours. The yields of the process are 30 to 40% of theory.

There has been no lack of attempts to prepare bis-triazolylstilbenedisulphonic acids of the formula (I) in higher yields and satisfactory purity from the bis-hydroxyiminohydrazones mentioned. However, when converted to a large industrial scale, the processes described below always entailed difficulties which considerably impaired economic utilisation of the compounds of the formula (I).

According to the process of DT-AS (German Published Specification) 1,670,914 (U.S. Pat. No. 3,666,758), the hydroxyiminohydrazones are heated to 130° to 165° C. in molten urea for 1.5 to 2 hours. The yields in the case of mono-triazolyl compounds, which without exception are satisfactory, are not achieved in the case of the bis-triazolylstilbenedisulphonic acids of the formula (I). This process has the disadvantages that considerable amounts of yellow by-products which contaminate the active compound are formed from the hydroxyiminohydrazones and their removal requires an expensive purification operation, and that the process liberates large amounts of ammonia, from the molten urea, which must be collected by additional off-gas washers.

This process could be improved by means of the variant of DT-OS (German Published Specification) No. 2,242,784 by carrying out the reaction with a smaller amount of urea in water or aqueous methanol. The process can indeed be more simply carried out and gives higher yields than the urea melt, but in this case also, the good yields on the laboratory scale cannot be transferred to large-scale industrial production.

Replacing urea by other acylating agents, such as have been proposed in DT-OS (German Published Specification) No. 2,210,261 (U.S. Pat. No. 3,965,094), using isocyanates and pyrocarbonic acid esters, indeed gives better yields in some cases, but the saving thereby achieved is more than compensated by the relatively high costs of the preparation of these acylating agents or of the removal of the by-products formed from these acylating agents.

There was therefore furthermore a need for an economic process for the preparation of the optical brighteners of the formula (I). It has now been found that bis-triazolylstilbene compounds of the formula (I) can be prepared on a large industrial scale in high purity, with a high yield and in an economic manner by a process in which hydroxyiminohydrazones of the formula

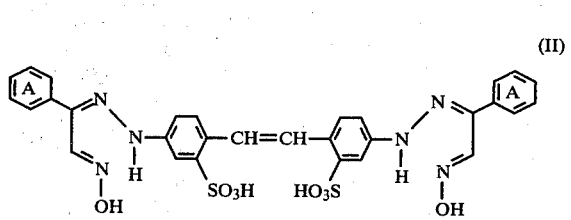

wherein
A can be substituted as indicated, are reacted with anhydrides of lower carboxylic acids in the presence of urea and polar solvents at temperatures from 10° to 60° C., preferably 25° to 45° C., and the reaction mixture is appropriately after-heated to 70° to 90° C.

The hydroxyiminohydrazones of the formula (II) are known. They are easily obtained by a condensation reaction of 4,4'-dihydrazinostilbene-2,2'-disulphonic acid with the corresponding hydroxyiminomethyl aryl ketones. In the process according to the invention, intermediate isolation of the hydroxyiminohydrazones thus prepared is not necessary, rather, after the condensation reaction has ended, the cyclisation can be carried out without interrupting the manufacturing operation.

Possible anhydrides of lower aliphatic carboxylic acids are simple and also mixed anhydrides of carboxylic acids with 1 to 4 C atoms, for example formic acid-acetic acid anhydride, propionic anhydride and, preferably, acetic anhydride.

The polar solvents can be alcohols, ethers, esters, carboxylic acid amides, sulphoxides, sulphones and phosphoric acid amides, for example dimethylformamide, dimethylsulphoxide, glycol methyl ether-acetate, glycol dimethyl ether, methanol, ethanol, n- and i-propanol, butanol, glycol, glycol monomethyl ether, glycol monoethyl ether, diglycol, diglycol monomethyl ether and monoethyl ether and triglycol and tetraglycol and monoalkyl ethers thereof.

In contrast to the processes of DT-AS (German Published Specification) No. 1,670,914 and DT-OS (German Published Specification) 2,242,784, the urea to be employed according to the invention does not act as an acylating agent under the reaction conditions present.

2 mols of anhydride are needed for the cyclisation of one mol of the compound of the formula (II); however, the cyclisation is appropriately carried out with an excess of anhydride, that is to say 2 to 4 mols of anhydride are employed per 1 mol of the compound (II) to be cyclised. Larger excesses do not interfere with the reaction, but for economic reasons are not advisable.

1 to 4 times the amount of a mixture of urea and the polar solvent, which consists of 10 to 90% by weight of urea and 90 to 10% by weight of the polar solvent, are used, relative to the amount of the hydroxyiminohydrazone. Furthermore, the reaction mixture can also contain up to 50% of water, relative to the amount of the hydroxyiminohydrazone. Higher proportions of water in the reaction mixture should be avoided so that the triazole yields are not perceptibly decreased. On the other hand, it is not absolutely necessary to carry out the reaction under anhydrous conditions, so that the precursors necessary for the preparation of the hydroxyiminohydrazone, that is to say dihydrazinostilbenedisulphonic acid and the particular hydroxyimino-ketone used, can be employed, without drying, as the still moist presspastes containing 20 to 30% of water, such as are obtained in their manufacture. In the case of starting materials containing a relatively high proportion of water, at least some of the water is stripped off under reduced pressure. The concentration of the hydroxyiminohydrazone in the cyclisation mixture is chosen as high as possible; it is only limited by the requirement of good thorough mixing and stirrability of the reaction mixture during the addition of the carboxylic acid anhydride. It is therefore particularly important to use a suitable effective stirrer. It is also possible, of course, to carry out the cyclisation under considerably more dilute conditions, increasing the product/solvent/urea ratio, without poorer yields or products which are less pure being obtained. Nevertheless, for economic reasons this is not advisable. The addition of effective emulsifiers, for example of the type of phenol polyglycol ethers, alkylated phenol polyglycol ethers and sulphuric acid half-esters thereof, can, however, be useful.

In carrying out the process according to the invention in practice, the procedure is, for example, to stir dihydrazinostilbenedisulphonic acid, in the form of a moist paste, into an initially introduced alcohol/urea mixture and, after determining the content of the mixture by analysis, adding the calculated amount of the hydroxyiminoketone. As soon as the condensation reaction has ended, the mixture is cooled to 20° to 35° C., whilst stirring, and the pH value is adjusted to a value between 7 and 10, preferably to about 8.0 to 8.5 (determined using a glass electrode) by adding alkali metal hydroxide solution dropwise. Whilst maintaining this pH value and the temperature, a slight excess of the carboxylic acid anhydride over the molar amount corresponding to the hydroxyimino-ketone is added dropwise, whilst stirring. Most of the hydroxyimino groups are thereby cyclised to the triazole; in order also to cyclise the last portions and furthermore to achieve a favourable crystal form which can be easily filtered, the mixture is warmed, after subsequently stirring for a short time, to 70° to 90° C., after adding water if desired. If a low-boiling alcohol, such as methanol or ethanol, is employed, this can be distilled off, appropriately over a separating column, during this procedure and re-used. The reaction product of the formula (I), which is present as an orange-yellow suspension, can then be easily isolated over a filter press. It is then purified in a known manner. Finally, depending on the intended use, it can be converted into the free acid or into another salt.

The compounds of the formula (I) and their alkali metal salts are valuable whiteners for textiles and washing agents.

EXAMPLE 1

80 kg of 70% pure 4,4'-dihydrazinostilbene-2,2'-disulphonic acid (moist press-paste) are added, with stirring, to 82 kg of diglycol methyl ether, which have been initially introduced into a heatable 1 m$^3$ VA kettle with an anchor stirrer extending to the wall. Thereafter, 82 kg of urea and 29 kg of anhydrous potassium acetate are added. As soon as a homogeneous suspension is present, 56.5 kg of 75% pure hydroxyiminoacetophenone (moist material on the filter) are added, with further stirring. The contents of the kettle are warmed to 50° C.; a pH value of 4.8 to 5.0 is gradually established. After applying a vacuum (about 25 mbars), most of the entrained water distils off. This temperature is maintained until the condensation reaction has ended (about 1 hour); finally, 1 kg of an aralkyl-phenol polyglycol ether-sulphonate, dissolved in 1.5 liters of water, are added, the orange-coloured suspension of the hydroxyiminohydrazone is subsequently cooled to 28° to 32° C. and the pH value is adjusted to 7.8 to 8.2 by adding 50% strength potassium hydroxide solution dropwise. Whilst maintaining this temperature (cooling) and pH values (dropwise addition of potassium hydroxide solution), 32 kg of acetic anhydride are allowed to run in gradually in the course of about 1½ hours, and the mixture is subsequently stirred for a further ½ hour. After allowing 500 liters of water to run in, the mixture is heated to 80° to 90° C. and subsequently stirred at this temperature for 1 to 2 hours. Thereafter, it is allowed to cool to 75° C., the contents of the kettle are pressed through a filter press and the material on the filter is rinsed with 300 liters of 3% strength potassium chloride solution and finally with 140 liters of water. About 300 kg. of a yellowish presspaste are obtained, which are purified in a known manner by recrystallising from hot aqueous dilute potassium hydroxide solution. After drying, 87.5 kg of the di-potassium salt of the formula (I) (ring A unsubstituted) are thus obtained as 93.5% pure material.

Yield: 83% of theory.

Similarly good results are obtained if diglycol methyl ether is replaced by the same amount of glycol dimethyl ether, glycol methyl ether-acetate or dimethylformamide.

EXAMPLE 2

400 g of 4,4'-dihydrazinostilbene-2,2'-disulphonic acid (100% pure) in the form of an approximately 75% pure paste are stirred into a mixture of 1 kg of urea and 1 liter of methanol, which has been initially introduced into a 10 liter glass flask provided with a highly efficient stirrer. First 185 g of sodium acetate and then 304 g of hydroxyiminoacetophenone (100% pure) in the form of approximately 80% pure moist material are introduced into the mixture. After stirring the mixture at 50° C. and at pH 4.7 to 5.0 (measured using a glass electrode) for about 2 hours, the condensation reaction has ended. The mixture is cooled to about 30° C. and the pH value is adjusted to 7.6 to 8.0 at this temperature with 50% strength potassium hydroxide solution. Whilst maintaining these conditions (external cooling, dropwise addition of potassium hydroxide solution), 240 g of acetic anhydride are added dropwise in the course of one hour, with thorough stirring. The mixture is further stirred for about 15 minutes, during which the orange-coloured reaction mixture remains very readily stirrable. Thereafter, 3 liters of water are allowed to run in, the pH being adjusted to 7.5 with potassium hydroxide solution, and the mixture is gradually warmed, with further stirring, up to 90° to 98° C., during which water-containing and ammonia-containing methanol, which can be re-used after a rectification, distils off. Finally, the mixture is allowed to cool to 80° to 85° C. and the orange-yellow product is filtered off on a suction filter and washed with 3 liters of 2% strength sodium chloride solution, and 1.5 liters of water are added. 2.4 kg of an aqueous paste are obtained which, for further purification, are dissolved at the boil in 8 liters of water, 20 ml of 40% strength sodium hydroxide solution being added. The solution is boiled under reflux cooling for 2 hours and 500 g of sodium chloride are then added. The mixture is then allowed to cool to 85° C. and the yellow crystals which have separated out are filtered off and washed with 3 liters of 1% strength sodium chloride solution. After drying, 590 g of the 91% pure di-sodium salt of the formula (I) (A is not substituted further), corresponding to a yield of 80% of theory, are obtained.

Similar results are obtained when about half of the potassium hydroxide solution is replaced by sodium hydroxide solution. If 336 g of p-methylhydroxyiminoacetophenone, 370 g of p-chlorohydroxyiminoacetophenone or 365 g of p-methoxyhydroxyiminoacetophenone are used instead of hydroxyiminoacetophenone, the relevant compounds of the formula (I) substituted in the p-position of A by methyl, chlorine or methoxy are obtained in comparable yields.

We claim:

1. In the reaction of a bis-hydroxyiminohydrazonostilbene compound of the formula

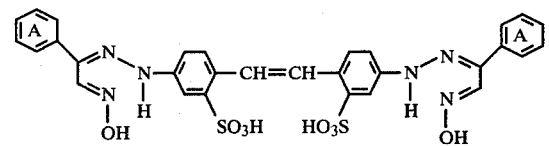

wherein
the phenyl radicals A can be substituted by halogen, $C_1$-$C_4$-alkyl or $C_1$-$C_4$-alkoxy,
with a cyclizing agent to produce the corresponding bis-triazolylstilbene compound of the formula

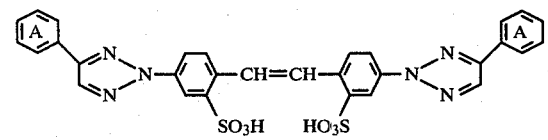

the improvement wherein the cyclizing agent is a lower carboxylic acid anhydride and the reaction is effected in the presence of urea and a polar solvent at from 10° to 60° C.

2. A process according to claim 1, wherein the temperature is from 25° to 45° C.

* * * * *